(12) United States Patent
Rao et al.

(10) Patent No.: US 7,645,890 B2
(45) Date of Patent: Jan. 12, 2010

(54) PROCESS FOR PREPARING DULOXETINE AND INTERMEDIATES FOR USE THEREIN

(75) Inventors: Dharmaraj Ramachandra Rao, Maharashtra (IN); Rajendra Narayanrao Kankan, Maharashtra (IN)

(73) Assignee: Cipla Limited, Mumbai (IN)

( * ) Notice: Subject to any disclaimer, the term of this patent is extended or adjusted under 35 U.S.C. 154(b) by 176 days.

(21) Appl. No.: 10/539,415

(22) PCT Filed: Dec. 10, 2003

(86) PCT No.: PCT/GB03/05357

§ 371 (c)(1),
(2), (4) Date: Mar. 20, 2006

(87) PCT Pub. No.: WO2004/056795

PCT Pub. Date: Jul. 8, 2004

(65) Prior Publication Data

US 2006/0205956 A1    Sep. 14, 2006

(30) Foreign Application Priority Data

Dec. 19, 2002    (GB) ................................. 0229583.0

(51) Int. Cl.
*C07D 333/22*    (2006.01)
(52) U.S. Cl. ...................................................... 549/76
(58) Field of Classification Search .................... 549/76
See application file for complete search history.

(56) References Cited

U.S. PATENT DOCUMENTS

| 3,830,806 | A | * | 8/1974 | Raabe et al. | 546/328 |
| 4,956,388 | A | * | 9/1990 | Robertson et al. | 514/651 |
| 5,362,886 | A | | 11/1994 | Berglund | |
| 6,162,949 | A | | 12/2000 | Gattuso | |
| 6,245,802 | B1 | | 6/2001 | Iyengar et al. | |
| 6,458,955 | B1 | | 10/2002 | Gattuso | |

FOREIGN PATENT DOCUMENTS

| EP | 0052492 | 5/1982 |
| EP | 0273658 | 7/1988 |
| EP | 0273658 | 10/1990 |
| EP | 0457559 | 11/1991 |
| WO | 0061540 | 10/2000 |
| WO | 03062219 | 7/2003 |

OTHER PUBLICATIONS

Wheeler et al., Jouurnal of labelled compounds and radiopharmaceuticals, 1995, vol. 36(3), pp. 213-223, abstract.*
J. Deeter et al.; Asymmetric Synthesis and Absolute Stereochemistry of LY248686; Tetrahedron Letters, vol. 31, No. 49, pp. 7101-7104, 1990; XP-001119089.
Chinese Office Action (Partial English Translation).
Kamal et al., Chemoenzymatic synthesis2 of both enantiomers of fluoxetine, tomoxetine and nisoxetine: lipase-catalyzed resolution of 3-aryl-3hydroxypropanenitriles, Tetrahedron: Asymmetry 13 (2002) 2039-2051.
Eliel et al., Stereochemistry of Organic Compounds, Separation of Stereoisomers Resolution. Racemization, Chapter 7 pp. 297-336, wiley, New York (1994).
Herr et al., Trip Report: Chiral USA, Boston Massachusetts, May 14-15, 2001, Albany Molecular Research, Inc. Technical Reports, vol. 6, No. 14, pp. 1-2, (2001).
Communication dated Oct. 30, 2007 in a related counterpart European Patent, 1,587,801, "Notice of Opposition to a European Patent," 16 pages.

* cited by examiner

*Primary Examiner*—Yong Chu
(74) *Attorney, Agent, or Firm*—Conley Rose, P.C.; Rodney B. Carroll

(57) ABSTRACT

A process for preparing (+)duloxetine, or an acid addition salt thereof, which process comprises resolving racemic(±)duloxetine with a chiral acid so as to obtain a salt of the chiral acid and (+)duloxetine, substantially free of (−)duloxetine; and (ii) if desired, converting the salt prepared in step (i) to the free base or another acid addition salt as appropriate. The process for preparing (+)duloxetine, or an acid addition salt thereof, can further comprise an O-alkylation intermediate process step which is carried out in the presence of a base and a phase transfer catalyst.

10 Claims, No Drawings

PROCESS FOR PREPARING DULOXETINE AND INTERMEDIATES FOR USE THEREIN

This application is a 35 U.S.C. §371 U.S. National Stage Application of International Application No. PCT/GB2003/005357, filed on Dec. 10, 2003, claiming the priority of Great Britain Application No. 0229583.0, filed Dec. 19, 2002, the entire disclosures of which are incorporated herein by reference in their entireties.

The present invention is concerned with a process for preparing duloxetine, in particular a process for preparing (+)duloxetine in enantiomerically pure form, and to intermediates for use therein.

Duloxetine, N-methyl-3-(1-naphthalenyloxy)-3-(2-thienyl)propanamine, is a dual serotonin and norepinephrine reuptake inhibitor. (+)Duloxetine has particular therapeutic utility as an anti-depressant.

Duloxetine, and the preparation thereof, is described in U.S. Pat. No. 5,023,269 and 4,956,388, and also Tetrahedron Letters, 31, (49), 7101-04, 1990. Seven different routes of synthesis have also been reported in Drugs of the Future 2000, 25(9) 907-916. These syntheses have involved either a resolution of a key intermediate or a stereospecific reduction of a keto group to the alcohol.

We have now observed that a particular chiral intermediate employed in the synthesis of (+)duloxetine, namely

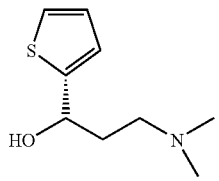

undergoes considerable racemisation during coupling with a 1-naphthyl halide under the reaction conditions employed in the prior art. In particular, in the presence of a strong base, such as sodium hydride, and a protic polar solvent, such as DMSO, the dimesyl anion can be generated which can cause partial or complete racemisation of the condensed product.

There is, therefore, a need for an improved process for the preparation of (+)duloxetine which alleviates the problems associated with prior art processes as referred to above. We have developed such a process which is advantageous in obviating racemisation, so as to yield an enantiomerically pure form of (+)duloxetine. In particular, our process can be seen to achieve the above described advantage, by carrying out resolution as a final step in the reaction process (thereby obviating the opportunity for racemisation during preceeding intermediate process steps) and/or avoiding conditions that would result in the production of intermediate products that would be prone to racemisation.

According to the present invention, therefore, there is provided a process for preparing (+)duloxetine, or an acid addition salt thereof, which process comprises:
 (i) resolving racemic (±)duloxetine with a chiral acid so as to obtain a salt of the chiral acid and (+)duloxetine, substantially free of (−)duloxetine; and
 (ii) if desired, converting the salt prepared in step (i) to the free base or another acid addition salt as appropriate.

The resolution step (i) is achieved with a suitable chiral acid in a suitable solvent. The chiral acid can typically be selected from the group consisting of mandelic acid, tartaric acid, di-p-toluyl tartaric acid, dibenzoyl tartaric acid, camphor sulfonic acid and the like. Other suitable chiral acids may be determined by testing and the use thereof in a process as described above falls within the scope of the present invention. Preferably the chiral acid employed in a process according to the present invention is (−)di-p-toluyl tartaric acid. Suitably, the solvent employed is a lower alkanol, such as methanol or ethanol, although again other suitable solvents can be determined by testing and the use thereof in a process as described above falls within the scope of the present invention. A preferred solvent is methanol.

The salts of (+)duloxetine prepared by resolution step (i) represent a further aspect of the present invention and there is further provided by the present invention, therefore, a salt of a chiral acid and (+)duloxetine, substantially free of (−)duloxetine. Such salts of a chiral acid and (+)duloxetine, substantially free of (−)duloxetine, are useful as intermediates for preparing the free base or another acid addition salt as appropriate.

Suitable salts provided by the present invention include (+)duloxetine mandelate, (+)duloxetine tartrate, (+)duloxetine di-p-toluyl tartrate, (+)duloxetine dibenzoyl tartrate, (+)duloxetine camphor sulfonate and the like. A preferred salt according to the present invention is (+)duloxetine di-p-toluyl tartrate, which is useful as an intermediate for preparing the free base or another acid addition salt as appropriate.

Intermediate salts prepared according to the present invention as described above can be converted to the free base or another acid addition salt according to step (ii) of a process according to the present invention. Suitably, an intermediate salt of the chiral acid and (+)duloxetine can be treated with a base, such as sodium hydroxide, to yield the free base. The free base itself can, if desired, be converted into an acid addition salt thereof.

Suitable acid addition salts which may be formed in step (ii) include those formed with pharmaceutically acceptable organic or inorganic acids and are well known to those of skill in the art. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, ∃-hydroxybutyrate, glycollate, maleate, tartrate, methanesulfonate, propanesulfonates, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and those formed with organic acids such as oxalic acid and maleic acid. A particularly preferred acid addition salt is the hydrochloride.

A particularly preferred process according to the present invention comprises:
 (i) resolving racemic (±)duloxetine with di-p-toluyl tartaric acid so as to obtain (+)duloxetine di-p-toluyl tartrate, substantially free of (−)duloxetine; and (ii) converting (+)duloxetine di-p-toluyl tartrate prepared in step (i) to (+)duloxetine hydrochloride.

A process according to the present invention preferably yields (+)duloxetine in substantially pure enantiomeric form. Thus the ratio of (+)duloxetine: (−)duloxetine as prepared by the present invention may be at least about 94:6, such as at least about 98:2, or more preferably at least about 99:1. Preferably (+)duloxetine prepared by a process according to the present invention has an enantiomeric purity of at least about 99%, or more particularly at least about 99.5%.

The proportion of (+)duloxetine achieved by a process according to the present invention can be increased by effecting one or more, for example two or three, recrystallisations in step (i). To this end, a crystalline salt obtained as a result of resolution may be dissolved in a solvent therefor and the salt recrystallised from the resulting solution. In this way the proportion of a salt with (+)duloxetine can thus be increased until it is substantially pure, that is substantially only a salt with (+)duloxetine is present.

The mother liquor from resolution step (i), or the mother liquor from the or each recrystallisation step, is enriched with (−)duloxetine. (−)Duloxetine present in one or more of these liquors, or the pooled liquors, may be converted into (±)duloxetine for reuse in a process according to the present invention substantially as hereinbefore described.

A further preferred aspect of a process according to the present invention comprises:

(i) resolving racemic (±)duloxetine with a chiral acid and obtaining a mother liquor enriched in (−)duloxetine;

(ii) converting (−)duloxetine obtained from step (i) to (±)duloxetine; and (iii) if desired, employing (±)duloxetine obtained from step (ii) in a process according to the present invention substantially as hereinbefore described.

Suitably, one or more mother liquors obtained from a process as described above, or pooled such mother liquors, may be treated with a base to remove any residual chiral acid and to thereby afford the free base enriched in (−)duloxetine. The free base can then be converted to the racemate, typically by reflux in a suitable solvent for several hours, optionally in the presence of a suitable acid (e.g. HCl) or a base (e.g. NaOH), which racemate can then be recycled for use in a process according to the present invention substantially as hereinbefore described.

Substantially as hereinbefore described an aim of a process according to the present invention is to obviate racemisation associated with prior art processes so as to yield an enantiomerically pure form of (+)duloxetine. According to the present invention this can be achieved by the resolution of (±)duloxetine as a final process step in the preparation of (+)duloxetine substantially as hereinbefore described, and according to a preferred aspect of the present invention the prior art techniques for the preparation of duloxetine can also be further modified by use of the following reaction conditions in an O-alkylation step employed in the synthesis of duloxetine. More particularly, an intermediate process step employed in a process according to the present invention comprises reacting intermediate compounds of formulae (I) and (II) so as to yield a compound of formula (III), or an acid addition salt thereof:

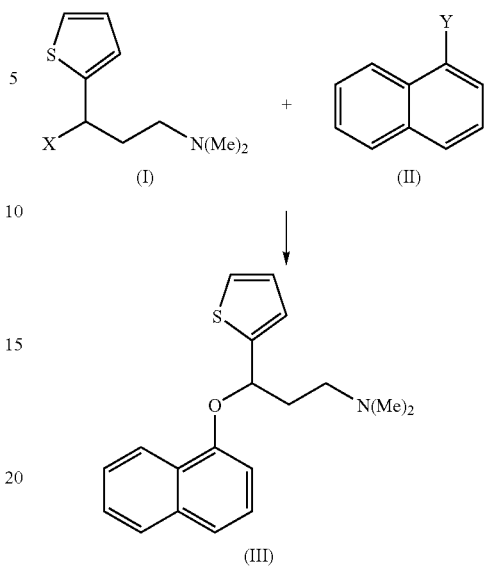

in the presence of a base and a phase transfer catalyst, where one of X and Y is hydroxy and the other is a leaving group. The use of such reaction conditions according to the present invention is advantageous in avoiding the use of stronger bases, such as sodium hydride, employed according to prior art preparatory techniques (such stronger bases being a fire hazard and also expensive), with the use of phase transfer catalysts facilitating the above reaction step to be carried out under milder conditions.

The use of the above reaction conditions can also offer advantages when chiral intermediates are employed in the synthesis of (+)duloxetine, by avoiding the considerable racemisation of the chiral intermediate (S)-2-(1-N,N-dimethyl-3-hydroxy)propyl amino)-thiophene seen during coupling thereof with a 1-naphthyl halide under the reaction conditions employed in the prior art. In particular, as previously discussed in the presence of a strong base, such as sodium hydride, and a protic polar solvent, such as DMSO, the dimesyl anion was generated under the prior art reaction conditions, which caused partial or complete racemisation of the condensed product. This undesirable racemisation can be avoided by carrying out the O-alkylation step under the reaction conditions of the present invention and there is, therefore, further provided a process for preparing (+)duloxetine, or an acid addition salt thereof, which comprises the following intermediate process step of reacting intermediate compounds of formulae (Ia) and (II) so as to yield a compound of formula (IIIa), or an acid addition salt thereof:

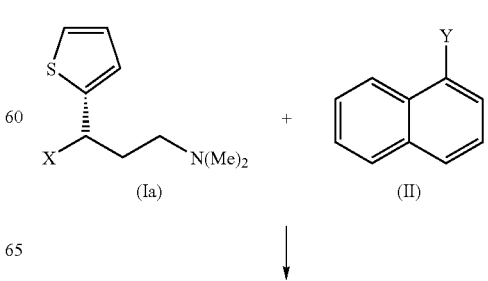

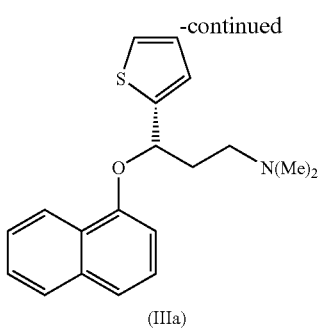

(IIIa)

Preferably the base employed can be an alkali metal hydroxide, an alkali metal carbonate, an alkali metal bicarbonate or the like. Suitably the base can be selected from the group consisting of potassium hydroxide, sodium hydroxide, potassium carbonate, sodium carbonate, sodium bicarbonate and the like. Potassium hydroxide can often be preferred.

Suitable phase transfer catalysts can be crown ethers, quaternary ammonium salts, quaternary phosphonium salts and the like. A preferred phase transfer catalyst can suitably be tetrabutyl ammonium bromide or 18-Crown-6.

A suitable leaving group as represented by X or Y can be p-toluenesulfonyl, methanesulfonyl, triphenylphosphine oxide, halo and the like, with halo being preferred.

Preferably X is hydroxy and Y is a leaving group such as halo, typically fluoro.

An intermediate of formula (III), or an acid addition salt thereof, is typically converted to (±)duloxetine by demethylating, typically in the presence of a reagent such a phenyl chloroformate or trichloroethyl chloroformate or the like to provide the corresponding intermediate, which is then hydrolysed to provide (±)duloxetine, or an acid addition salt thereof. An intermediate of formula (IIIa), or an acid addition salt thereof, is similarly typically converted to (+)duloxetine, or an acid addition salt thereof, by demethylating, typically in the presence of a reagent such a phenyl chloroformate or trichloroethyl chloroformate or the like to provide the corresponding intermediate, which is then hydrolysed to provide (+)duloxetine, or an acid addition salt thereof.

A further preferred process according to the present invention comprises reacting intermediate compounds of formulae (I) and (II) to yield an intermediate compound of formula (III), or an acid addition salt thereof, demethylating a compound of formula (III), or an acid addition salt, so as to yield (±)duloxetine and converting (±)duloxetine to (+)duloxetine, or an acid addition salt thereof, employing a process according to the present invention substantially as hereinbefore described. A still further preferred process according to the present invention comprises reacting intermediate compounds of formulae (Ia) and (II) to yield an intermediate compound of formula (IIIa), or an acid addition salt thereof, demethylating a compound of formula (IIIa), or an acid addition salt, so as to yield (+)duloxetine, or an acid addition salt thereof.

A particularly preferred process according to the present invention comprises reacting intermediate compounds of formulae (I) and (II) where X is hydroxy and Y is fluoro, followed by oxalic acid to yield an oxalate salt of intermediate compound of formula (III), demethylating the intermediate compound of formula (III) so as to yield (±)duloxetine and converting (±)duloxetine to (+)duloxetine employing a process according to the present invention substantially as hereinbefore described. In particular it is especially preferred that resolution to yield (+)duloxetine comprises:

(i) resolving racemic (±)duloxetine with (−)di-p-toluyl tartaric acid so as to obtain (+)duloxetine di-p-toluyl tartrate, substantially free of (−)duloxetine; and (ii) converting (+)duloxetine di-p-toluyl tartrate prepared in step (i) to (+)duloxetine hydrochloride.

The compounds employed as starting materials in the processes of the present invention can be prepared by standard procedures known in the art.

The present invention further provides (+)duloxetine, or an acid addition salt thereof, obtained by a process substantially as hereinbefore described. Such (+)duloxetine, or an acid addition salt thereof, according to the present invention can suitably be formulated to provide a pharmaceutical composition according to the present invention, and there is further provided by the present invention a pharmaceutical composition comprising (+)duloxetine, or an acid addition salt thereof, obtained by a process substantially as hereinbefore described.

The present invention will now be illustrated by the following Examples, which do not limit the scope of the invention in any way.

EXAMPLE 1

N,N-dimethyl-?-(1-naphthalenyloxy)-2-thiophenepropanamine oxalate 2-(1-N,N-dimethyl-3-hydroxy)propyl amino)-thiophene (12.4 gms) was dissolved in DMSO (70 ml). Potassium hydroxide (18.7 gms) and tetrabutyl ammonium bromide were added (0.1 gms). The reaction mixture was stirred at 60EC for 1 hour and 4-fluoro naphthalene (11.7 gms) was added slowly over 2 hours. After the reaction was complete, it was quenched in ice-water and extracted into toluene. The toluene layer was dried and concentrated under vacuum. The residue was dissolved in 100 ml of ethyl acetate and oxalic acid (7 gms) was added. The reaction mixture was stirred for 1 hour and filtered (15.5 gms, 76% yield).

EXAMPLE 2

(±)-N-methyl-?-(1-naphthalenyloxy)-2-thiophenepropanamine ((±) Duloxetine)

N,N-dimethyl-?-(1-naphthalenyloxy)-2-thiophenepropanamine (50 gms) was dissolved in toluene (250 ml). To the reaction mixture was added diisopropyl ethyl amine (24.8 gms) and phenyl chloroformate (30 gms) was added slowly. The reaction mixture was heated to 60EC and stirred for 2 hours. After completion of the reaction, the mixture was quenched in 50 ml of 5% sodium bicarbonate solution. The toluene layer was separated, dried and concentrated to give a residue.

The residue was dissolved in a mixture of DMSO and water. To this was added sodium hydroxide (22 gms) and the reaction mixture refluxed for 8 hours. The reaction was then diluted with 700 ml of water and extracted with ethyl acetate. The ethyl acetate layer was dried and concentrated to give the title compound (74%).

EXAMPLE 3

(+)-N-methyl-?-(1-naphthalenyloxy)-2-thiophenepropanamine ((±) Duloxetine)

(±) Duloxetine (20 gms) was dissolved in methanol (20 ml) and (−)di-p-toluyl tartaric acid (6.5 gms) was added. The reaction was stirred under reflux for 1 hour, methanol concentrated under vacuum, acetone (150 ml) charged and cooled to 5EC. The solids obtained were filtered and dried under vacuum at 40EC to give the (−)di-p-toluyl tartrate salt of (+) duloxetine (12.5 g).

The above tartrate salt was suspended in a mixture of water and toluene and 500 mg of sodium hydroxide was added under stirring. The toluene layer was separated, dried and concentrated under vacuum to residue. Ethyl acetate (20 ml) was added to the residue followed by oxalic acid (2.2 gms). The reaction was cooled to 5EC and the mixture stirred for 1 hour. The solids were filtered and dried under vacuum at 40EC to yield the title compound as an oxalate (6.5 gms).

The methanolic mother liquor obtained after filtration of the (−)DPTA salt of (+)duloxetine was basified to pH 10 by lye solution (50% NaOH) and heated to reflux for 10 hours. Extractions with dichloromethane (100 ml) followed by concentration of the solvent yielded the racemate base (8.5 gm) having enantiomeric ratio (+/−) of 48:52 by chiral HPLC.

EXAMPLE 4

(S)-N,N-dimethyl-?-(1-naphthalenyloxy)-2-thiophenepropanamine oxalate (S)-2-(1-N,N-dimethyl-3-hydroxy)propyl amino)-thiophene (12.5 gms) was dissolved in DMSO (60 ml). Potassium hydroxide (20.5 gms) and 18-Crown-6 were added (0.12 gms). The reaction mixture was stirred at 60° C. for 1 hour and 4-fluoro naphthalene (11.9 gms) was added slowly over 2 hours. After the reaction was complete, it was quenched in ice-water and extracted into toluene. The toluene layer was dried and concentrated under vacuum. The residue was dissolved in 100 ml of ethyl acetate and oxalic acid (7.5 gms) was added. The reaction mixture was stirred for 1 hour and filtered to give the title compound in 88% yield.

EXAMPLE 5

(+)-N-methyl-?-(1-naphthalenyloxy)-2-thiophenepropanamine hydrochloride ((+) Duloxetine hydrochloride)

(S)-N,N-dimethyl-?-(1-naphthalenyloxy)-2-thiophenepropanamine oxalate (50 gms) was dissolved in water. The pH of the solution was adjusted to between 9-10 with 5% sodium hydroxide. The mixture was extracted with toluene. The toluene layer was concentrated under vacuum to about 250 ml. To the reaction mixture was added ?-chloroethyl chloroformate (30 gms) slowly. The reaction mixture was heated to 60° C. and stirred for 2 hours. After completion of the reaction, the mixture was concentrated under vacuum to a residue. The residue was dissolved in methanol and refluxed for 2 hours. The reaction mixture was concentrated under vacuum to give a solid residue which was triturated with acetone to give the title compound (36 gms).

The invention claimed is:

1. A process for preparing (+)duloxetine, or an acid addition salt thereof, which process comprises:
   (i) resolving racemic (±)duloxetine with di-p-toluyl tartaric acid in a lower alkanol solvent so as to obtain a salt of the di-p-toluyl tartaric acid and (+)duloxetine, substantially free of (−)duloxetine wherein the ratio of (+) duloxetine: (−) duloxetine is at least about 94:6: and
   (ii) if desired, converting the salt prepared in step (i) to the free base or a further acid addition salt.

2. A process according to claim 1, wherein step (ii) comprises reacting a salt prepared in (i) with hydrochloric acid to yield (+)duloxetine hydrochloride.

3. A process for preparing (+)duloxetine hydrochloride which process comprises:
   (i) resolving racemic (±)duloxetine with di-p-toluyl tartaric acid in a lower alkanol solvent so as to obtain (+)duloxetine di-p-toluyl tartrate, substantially free of (−)duloxetine wherein the ratio of (+) duloxetine (−) duloxetine is at least about 94:6; and
   (ii) converting (+)duloxetine di-p-toluyl tartrate prepared in step (i) to (+)duloxetine hydrochloride.

4. A process which comprises:
   (i) resolving racemic (±)duloxetine with a di-p-toluyl tartaric acid in a lower alkanol solvent in a process according to claim 1, and obtaining a mother liquor enriched in (−)duloxetine;
   (ii) converting (−)duloxetine obtained from step (i) to (±)duloxetine; and
   (iii) if desired, employing (±)duloxetine obtained from step (ii) in a process according to claim 1.

5. The process of claim 1 wherein the lower alkanol solvent comprises ethanol or methanol.

6. The process of claim 1 wherein the lower alkanol solvent is methanol.

7. The process of claim 3 wherein the lower alkanol solvent comprises ethanol or methanol.

8. The process of claim 3 wherein the lower alkanol solvent is methanol.

9. The process of claim 4 wherein the lower alkanol solvent comprises ethanol or methanol.

10. The process of claim 4 wherein the lower alkanol solvent is methanol.

* * * * *